United States Patent
Yokoi et al.

(10) Patent No.: US 8,796,010 B2
(45) Date of Patent: Aug. 5, 2014

(54) ISOLATOR FOR CELL CULTURE

(75) Inventors: Yasuhiko Yokoi, Ota (JP); Akifumi Iwama, Tukuba (JP); Shinji Fukui, Oura (JP); Atsushi Nakao, Neyagawa (JP); Hiroshi Yamamoto, Neyagawa (JP); Jirou Ohnishi, Ota (JP); Hironobu Sunayama, Kanazawa (JP); Kanjun Yamamoto, Kanazawa (JP)

(73) Assignees: Panasonic Healthcare Co., Ltd., Ehime (JP); Shibuya Kogyo Co., Ltd., Ishikawa (JP)

( * ) Notice: Subject to any disclaimer, the term of this patent is extended or adjusted under 35 U.S.C. 154(b) by 687 days.

(21) Appl. No.: 13/035,538

(22) Filed: Feb. 25, 2011

(65) Prior Publication Data

US 2011/0212513 A1    Sep. 1, 2011

(30) Foreign Application Priority Data

Feb. 26, 2010    (JP) .................. 2010-043551

(51) Int. Cl.
    *C12M 1/38* (2006.01)
    *C12M 1/12* (2006.01)
    *C12M 1/00* (2006.01)

(52) U.S. Cl.
    CPC .............. *C12M 37/04* (2013.01); *C12M 37/00* (2013.01); *C12M 41/14* (2013.01); *Y10S 435/809* (2013.01)
    USPC ..................... 435/286.6; 435/303.1; 435/809; 422/565

(58) Field of Classification Search
    USPC ..................... 435/303.1, 809, 286.6; 422/565
    See application file for complete search history.

(56) References Cited

U.S. PATENT DOCUMENTS 3,021,776 A * 2/1962 Kennedy .................. 454/57
4,262,091 A    4/1981 Cox
(Continued)

FOREIGN PATENT DOCUMENTS

GB    2 407 048 A    4/2005
JP    09168992 A    6/1997
(Continued)

OTHER PUBLICATIONS

Korean Office Action, and English translation thereof, issued in Korean Patent Application No. 10-2011-0017069 dated Jun. 8, 2012.

(Continued)

*Primary Examiner* — William H Beisner
(74) *Attorney, Agent, or Firm* — McDermott Will & Emery LLP

(57) ABSTRACT

An isolator for cultivating cells including a working chamber having a plurality of gloves arranged side by side into which operator's hands are inserted to operate cells, the working chamber being sectioned into at least an operation area for operating the cells, and an auxiliary working area for opening a packaged auxiliary instrument used to operate the cells, a gas supply unit that supplies gas into the working chamber so that the gas flows downwardly from an upper side in the working chamber, and a gas flow control unit for controlling the flow of the downwardly flowing gas so that the gas flows from the operation area to the auxiliary working area around the gloves, wherein the gas flow control unit has an exhaust hole portion that has an opened area for passing the gas therethrough and is provided at a lower portion of at least the auxiliary working area, and through which the gas in the auxiliary working area is exhausted.

20 Claims, 16 Drawing Sheets

(56) References Cited

U.S. PATENT DOCUMENTS

| | | | |
|---|---|---|---|
| 5,356,335 A * | 10/1994 | Matsui et al. | 454/52 |
| 5,851,143 A * | 12/1998 | Hamid | 454/57 |
| 5,997,399 A | 12/1999 | Szatmary | |
| 2008/0213873 A1 | 9/2008 | Murray et al. | |

FOREIGN PATENT DOCUMENTS

| | | |
|---|---|---|
| JP | 2001-518816 | 10/2001 |
| JP | 2009-225742 A | 10/2009 |
| JP | 2009-226048 A | 10/2009 |
| KR | 2007-0120636 A | 12/2007 |
| WO | WO 98/44958 | 10/1998 |

OTHER PUBLICATIONS

Extended European Search Report issued in European Patent Application No. EP 11155815.1 dated Aug. 5, 2011.

* cited by examiner

US 8,796,010 B2

ISOLATOR FOR CELL CULTURE

INCORPORATION BY REFERENCE

The present application claims priority under 35 U.S.C. §119 to Japanese Patent Application No. 2010-043551 filed on Feb. 26, 2010. The content of the application is incorporated herein by reference in its entirety.

BACKGROUND OF THE INVENTION

1. Field of the Invention

The present invention relates to an isolator for cell culture (cultivation).

2. Description of Related Art

An isolator containing a working chamber under a sterile environment has been used (for example, see JP-T-2001-518816; the term "JP-T" as used herein means a published Japanese translation of a PCT patent application). In the isolator, a culturing work for culture, operation, observation, etc. of cells of human bodies, animals or plants or microorganisms is performed by a worker.

In some cases, an auxiliary work such as an opening work, a seal-breaking work, etc. of instruments for experiments and chemicals is performed in an isolator. Therefore, when this auxiliary work is performed, dust or dirt occurs in some cases. Therefore, when the auxiliary work is performed, dust or dirt occurs and invades into cells or the like, whereby a culturing work is adversely affected.

SUMMARY OF THE INVENTION

In order to attain the above object, according to the present invention, an isolator for cultivating cells, comprises: a working chamber having a plurality of gloves arranged side by side into which operator's hands are inserted to operate cells, the working chamber being sectioned into at least an operation area for operating the cells, and an auxiliary working area for opening a packaged auxiliary instrument used to operate the cells; a gas supply unit that supplies gas into the working chamber so that the gas flows downwardly from an upper side in the working chamber; and a gas flow control unit for controlling the flow of the downwardly flowing gas so that the gas flows from the operation area to the auxiliary working area around the gloves (particularly in the neighborhood of the gloves), wherein the gas flow control unit has an exhaust hole portion that has an opened area for passing the gas therethrough and is provided at a lower portion of at least the auxiliary working area, and through which the gas in the auxiliary working area is exhausted.

In the above isolator, the exhaust hole portion is provided to each of the operation area and the auxiliary working area, and the opened area of the exhaust hole portion at the auxiliary working area side is set to be larger in total opening area than the opened area of the exhaust hole portion at the operation area side.

The above isolator further comprises an air supply port that exhausts the gas from the exhaust hole portion and is disposed at the auxiliary working area side.

In the above isolator, the air supply port serves as an air supply port of an exhaust duct for exhausting the gas from the exhaust hole portion.

The above isolator further comprises an exhaust blower for exhausting the gas from the exhaust hole portion, wherein the air supply port serves as an air supply port of the exhaust blower, and the exhaust blower is provided below the lower portion of the auxiliary working area.

In the above isolator, the exhaust hole portion is provided to each of the operation area and the auxiliary working area, and the opening area of the opened area of the exhaust hole portion at the lower portion of the auxiliary working area is set to be equal to the opening area of the opened area of the exhaust hole portion at the operation area side.

In the above isolator, the exhaust hole portion comprises a belt-like member that extends in a width direction of the working chamber and has a plurality of holes formed therein.

The above isolator further comprises a cultivating chamber for cell culture that is disposed to be adjacent to the operation area.

According to the isolator of the present invention, contamination of dirt or dust into cells or the like can be prevented, and thus dirt or dust can be prevented from affecting the cultivation (culture) work such as the operation, etc. of cells or the like can be prevented.

DETAILED DESCRIPTION OF THE PREFERRED EMBODIMENTS

Preferred embodiments according to the present invention will be described hereunder with reference to the accompanying drawings.

First Embodiment

Figure 1:
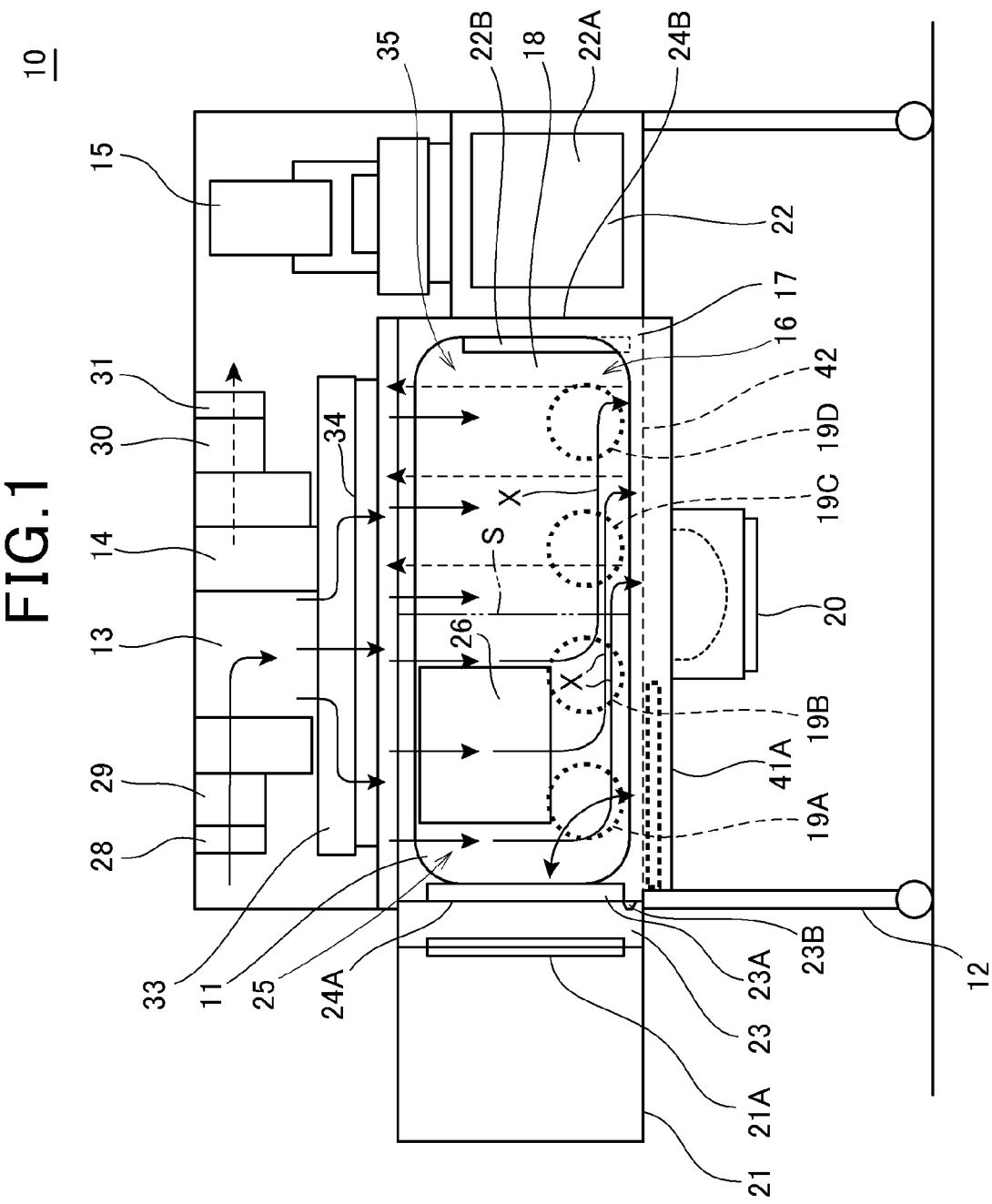
FIG. 1 is a front view showing an isolator according to a first embodiment of the present invention.

FIG. 1 is a front view showing an isolator according to a first embodiment of the present invention.

As shown in FIG. 1, an isolator 10 has a glove box 11 whose inside is kept under sterile conditions, a frame 12 for supporting the glove box 11 from the lower side, an air supply blower 13 and an exhaustion blower 14 which are provided on the top surface of the glove box 11, and a decontamination unit for decontaminating the inside of the glove box 11 with decontamination gas.

The inner space of the glove box 11 serves as a working chamber 16 in which works for biological derivative materials as targets such as a cell extraction work, a cell culturing work, etc. are performed. The glove box 11 has a box-shaped housing 17 which is opened at one surface thereof, and a transparent plate 18 which is formed of a rectangular glass or resin member and closes the opening of the housing 17. The inside of the working chamber 16 is visually identified through the transparent plate 18 which is provided to the substantially overall front surface of the glove box 11. The glove box 11 is designed in a rectangular shape which is longest in the width direction thereof.

The transparent plate 18 is provided with plural gloves 19A, 19B, 19C, 19D extending into the working chamber 16, and a worker for operating and cultivating cells, etc. can perform works in the working chamber 16 by inserting his/her hands from the outside into the gloves 19A, 19B, 19C, 19D. Each of the gloves 19A, 19B, 19C, 19D is disposed at a lower position than the intermediate portion of the glove box 11 in height. In this embodiment, four gloves 19A, 19B, 19C and 19D are horizontally arranged substantially side by side on a line so as to be spaced from one another at a substantially equal interval. That is, in the glove box 11, the four gloves 19A, 19B, 19C and 19D are arranged side by side laterally in the glove box 11, and thus two workers can perform works at the same time by inserting their both hands into the gloves 19A, 19B, 19C and 19D. The glove box 11 contains an incubator 21 (cultivating chamber) for cultivating cells accommodated therein, a pass box 22 through which articles (samples) are inserted into and taken out from the working chamber 16, a joint box 23 to which the incubator 21 is secured, and a centrifugal machine 20.

The joint box 23 is provided to one side surface 24A at one end side in the width direction of the glove box 11, and has a joint box door 23A for blocking a part of the one side surface 24A so that the one side surface 24A is freely opened or closed. The incubator 21 is freely detachably secured to the joint box 23.

The incubator 21 is a box-shaped cultivating chamber in which an environment suitable for cultivating cells is formed. The incubator 21 is designed so that the temperature and $CO_2$ concentration in the incubator 21 can be adjusted, and it has a function of decontaminating the inside thereof. The incubator 21 is provided with a door 21A for closing the inside of the incubator 21 so that the inside of the incubator 21 can be hermetically sealed. The incubator 21 is secured to the joint box 23 from the outside under the state that the door 21A faces the joint box door 23A. When the worker accesses the incubator 21 from the inside of the working chamber 16, the worker opens the joint box door 23A, opens the door 21A and then extends his/her hand to insert or take out cells accommodated in petri dish or like into/from the incubator 21. Furthermore, under the state that the incubator 21 is detached from the joint box 23, the joint box door 23A is closed, and the hermetic sealing state between the inside of the working chamber 16 and the outside of the working chamber 16 is kept.

The pass box 22 is a front chamber used when articles are inserted into or taken out from the glove box 11. The pass box 22 has an external door 22B provided to the front surface side of the glove box 11 so as to be freely openable and closable, and an internal door 22B for closing a part of the side surface of the glove box 11 so that the part can be freely opened/closed. The pass box 22 is provided to the other side surface 24B at the other end side in the width direction of the glove box 11. Furthermore, the pass box 22 is connected to a decontamination unit 15.

When an article is carried into the glove box 11, the external door 22A is opened, the article is put into the pass box 22 and then the external door 22A is closed. Under this state, the article is decontaminated by the decontamination unit 15. Thereafter, the internal door 22B is opened by using the gloves 19C and 19D, and the article is taken out from the pass box 22, whereby the article can be carried into the glove box 11.

Articles which are to be carried into the glove box 11 by using the pass box 22 contain instruments, etc. used for cultivating works, and for example, an injector is used as an article. The instruments such as injectors, etc. are accommodated in packages which are managed under a sterile condition.

The glove box 11 is sectioned into an operation area 25 in which cultivating works such as cultivation, operation, observation, etc. of cells are performed, and an auxiliary working area 35 in which auxiliary works for the cultivating work are performed. An opening work for opening packages for instruments and chemicals used for the cultivating work, an operation of the centrifugal machine 20, etc. are performed as the auxiliary works.

Specifically, the operation area 25 is one half side portion at one side of the glove box 11 at which the incubator 21 is disposed, and the auxiliary working area is the other half side portion at the other side of the glove box 11 at which the pass box 22 is disposed. The boundary portion S between the operation area 25 and the auxiliary working area 35 is located at the intermediate portion between the two gloves 19B and 19C at the center side as indicated by two-dotted chain line extending in the vertical direction of FIG. 1. That is, the two gloves 19A and 19b at the incubator 21 side are used for the works to be performed in the operation area 25, and the two gloves 19C and 19D at the pass box 22 side are used for the works to be performed in the auxiliary working area 35. A worker may insert his/her right and left hands into the two gloves 19B and 19C at the center portion and perform a work over the operation area 25 and the auxiliary working area 35 by using both the right and left hands.

In this embodiment, the half side portion (the left side portion in FIG. 1) of the working chamber 16 at the incubator 21 side is used as the operation area 25 for performing the cultivating work such as the operation, etc. of cells, and thus the cells used in the cultivating work can be directly carried into the incubator 21 by using the gloves 19A and 10B, so that the workability can be enhanced. Furthermore, the other half side portion (the right side portion in FIG. 1) of the working chamber 16 at the pass box 22 side is used as the auxiliary working area 35, and thus the instruments, etc. which are taken out from the bass box 22 can be opened and supplied to the operation area 25 by using the gloves 19C and 19D, so that the workability is enhanced.

The centrifugal machine 20 is used for a work of separating cells, etc., and disposed at the intermediate portion in the width direction of the glove box 11. Therefore, the centrifugal machine 20 can be used from both the sides of the operation area 25 side and the auxiliary working area 35 side.

Furthermore, the operation area 25 of the glove box 11 is provided with a display 26. The display 26 is provided so as to face the transparent plate 18, and it can display a working procedure of the cultivating work, etc. to the worker.

Figure 2:
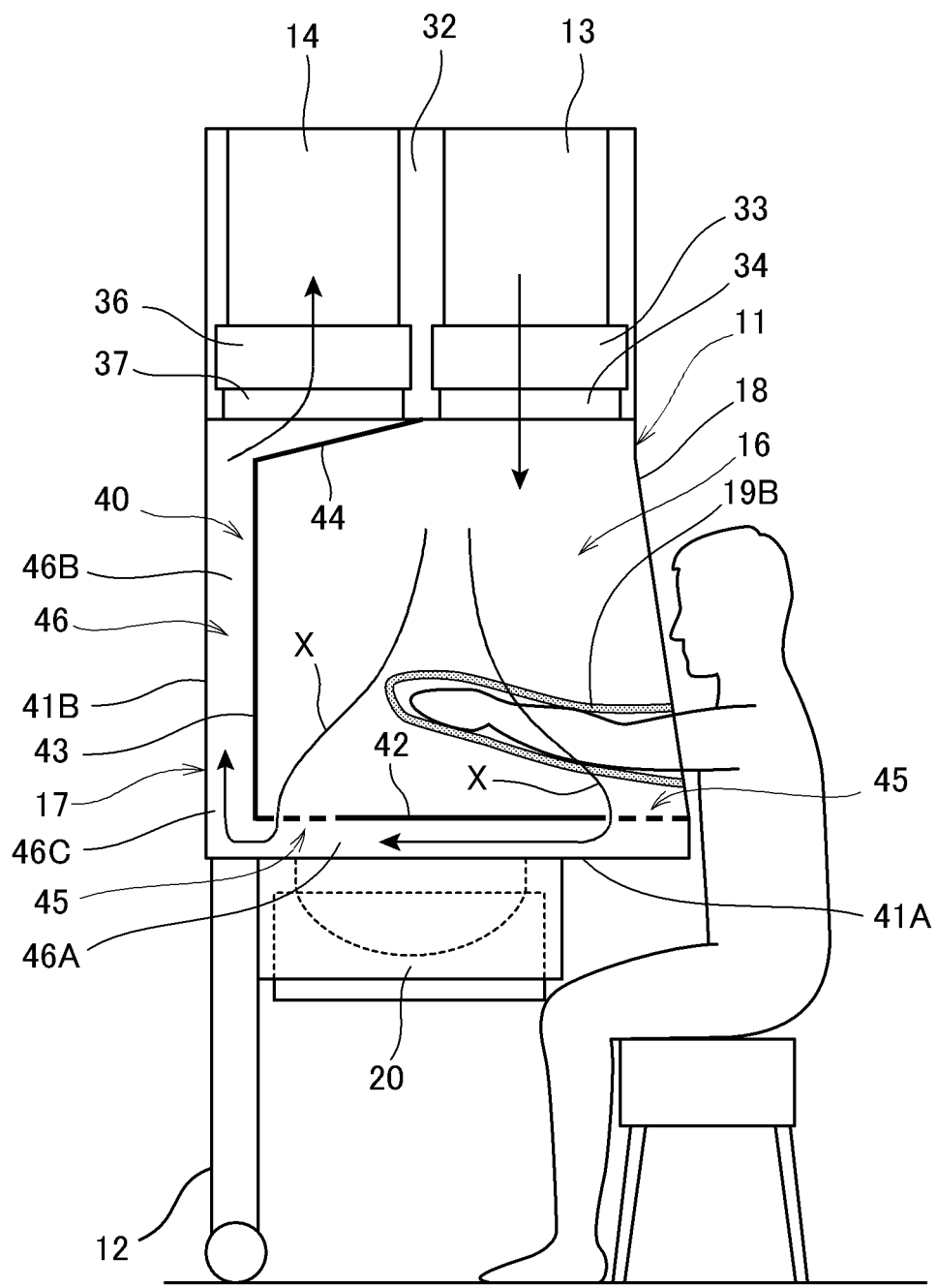
FIG. 2 is a side cross-sectional view of the isolator.

FIG. 2 is a side cross-sectional view showing the isolator 10.

As shown in FIGS. 1 and 2, the air supply (air suction) blower 13 and the exhaust blower 14 are provided above the glove box 11 to be arranged in the front-and-rear direction. The air supply blower 13 is disposed at the front portion of the transparent plate 18 side, and the exhaust blower 14 is disposed at the rear portion of the transparent plate 18 side. An air supply blower catalysis 28 and an air supply valve 29 for adjusting an air supply (intake) amount are connected to the air supply blower 13. An exhaust catalysis 31 for purifying exhaust gas discharged to the outside and an exhaust valve 30 for adjusting an exhaust gas amount are connected to the exhaust blower 14.

The air supply blower 13 and the exhaust gas blower 14 are insulated from each other by a partition portion 32 extending in the vertical direction (FIG. 2). An air supply chamber 33 extending substantially wholly in the width direction of the glove box 11 is disposed below the air supply blower 13, and an air supply filter 34 for collecting dust in sucked gas (air or the like) is provided between the air supply chamber 33 and the working chamber 16. Furthermore, an exhaust chamber 36 extending substantially wholly in the width direction of the glove box 11 is provided below the exhaust blower 14, and an exhaust filter 37 for collecting dust in exhaust gas (air or the like) is provided between the exhaust chamber 36 and the working chamber 16.

An inner wall plate 40 extending substantially wholly in the width direction of the inside of the glove box 11 is provided to partition the inside of the glove box 11. A space is formed at the lower portion and back surface portion of the inside of the glove box 11 by the inner wall plate 40. The inner wall plate 40 is formed as if one plate member is bent, and it is constructed to have a working plate 42 (lower surface) which is disposed to be spaced from the bottom surface of the housing 17 and constitutes the bottom surface portion of the working chamber 16, a back surface plate 43 which is disposed to be spaced from the back surface 41B of the housing 17 and constitutes the back surface of the working chamber 16, and a partition plate 44 for connecting the upper end of the back surface plate 43 and the upper surface of the working chamber 16.

The working plate 42 is provided substantially in parallel to the bottom surface 41A, and an exhaust hole portion 45 extending in the width direction of the glove box 11 is formed in each of the front and rear edges of the working plate 42. The back surface plate 43 is continuous with the rear edge of the working plate 42 and extends upwardly in parallel to the back surface 41B. The partition plate 44 extends obliquely from the upper edge of the back surface plate 43 to the front surface side, and also is connected to the lower surface of the partition portion 32. The space surrounded by the working plate 42, the back surface plate 43, the partition plate 44, and the bottom surfaces 41A and the back surface 41B of the housing 17 functions as an exhaust gas passage 46, and the exhaust gas from the working chamber 16 passes through the exhaust gas passage 46 and flows to the exhaust blower 14 side. The exhaust gas passage 46 has a lower duct 46 extending at the lower side of the working plate 42 and an upper duct 46B (exhaust duct) which is continuous with the lower duct 46A and extends upwardly between the back surface 41B of the housing 17 and the back surface plate 43. The lower end of the upper duct 46B serves as an air supply port 46C of the upper duct 46B.

Air (gas) at the outside of the glove box 11 passes through the air supply catalyst 28, invades into the air supply chamber 33 through the air supply valve 29, prevails over the whole area of the air supply chamber 33 in the width direction, passes through the air supply filter 34 so that dust in the air (gas) is removed, and then flows into the working chamber 16 from the upper side. The air (gas) flowing into the working chamber 16 flows from the upper side to the lower side over the whole area of the working chamber 16 in the width direction, reaches the lower duct 46A through the exhaust hole portions 45 of the front and rear edges of the working plate 42, flows upwardly in the upper duct 46B, passes through the exhaust gas filter 37 and then flows into the exhaust chamber 36. The air (gas) flowing into the exhaust chamber 36 is sucked by the exhaust blower 14, passed through the exhaust valve 30 and the exhaust catalyst 31 and then discharged to the outside.

Figure 3:
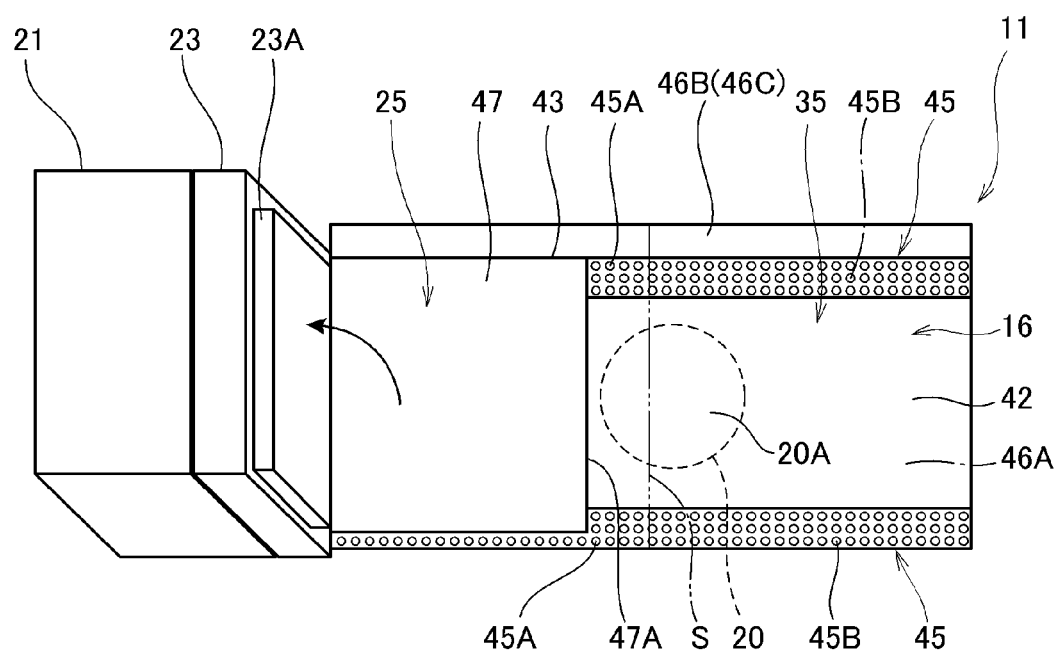
FIG. 3 is a top view of the inside of a working chamber.
Figure 4:
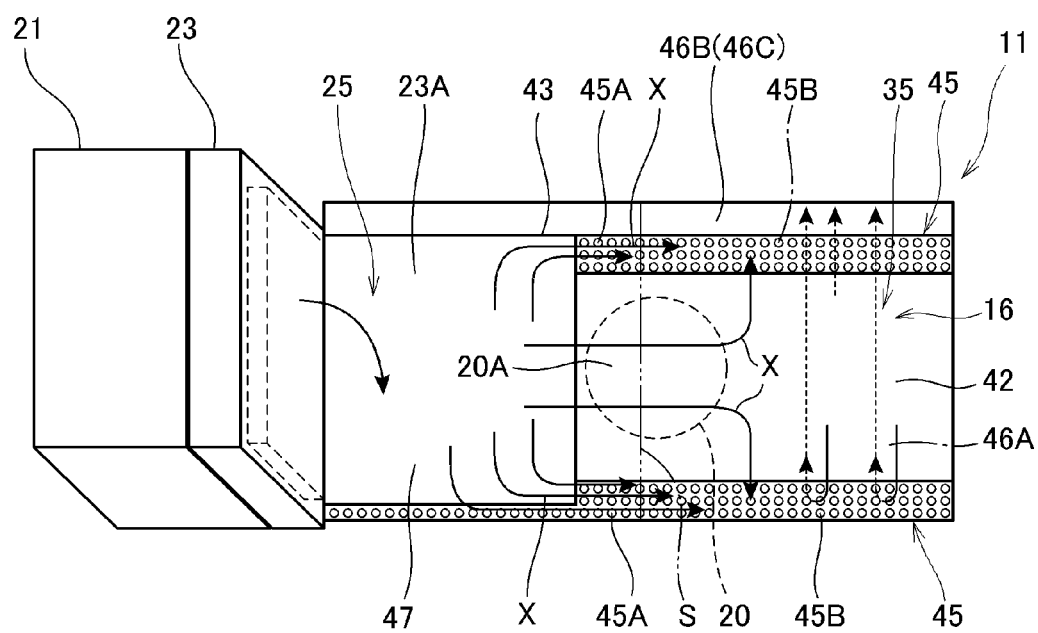
FIG. 4 is another top view of the inside of the working chamber.

FIGS. 3 and 4 are top views of the inside of the working chamber 16. FIG. 3 shows a state that the joint box door 23A is closed, and FIG. 4 shows a state that the joint box door 23A is opened.

The joint box door 23A has a hinge 23B (FIG. 1) at the lower edge thereof, and it is downwardly laid toward the working chamber 16 side around the hinge 23B, whereby the opening state is set.

As shown in FIG. 3, a substantially rectangular door mount recess portion 47 which is concaved downwardly is formed on the working plate 42 at the operation area 25 side. The door mount recess portion 47 is formed in conformity with the joint box door 24A, and when the joint box door 23A is set to the open state, the joint box door 23A is mounted in the door mount recess portion 47 as shown in FIG. 4. Under the state that the joint box door 23A is mounted in the door mount recess portion 47, the upper surface of the joint box door 23A is coincident with the upper surface of the working plate 42 in height, and thus the joint box door 23A serves as a part of the working plate 42.

That is, when a cultivating work is performed, the joint box door 23A is used under the open state, and functions as a working table. The cultivating work is mainly performed on the joint box door 23A. As described above, the joint box door 23A is downwardly laid to be set to the open state, and mounted in the door mount recess portion 47. Therefore, the joint box door 23A can be prevented from obstructing the display of the display 26, and also the joint box door 23A can be used as a working table.

A wall portion is provided between the door mount recess portion 47 and the lower duct 46A, and thus the door mount recess portion 47 does not directly intercommunicate with the lower duct 46A.

The centrifugal machine 20 is covered by an lid portion 20A which is freely openable and closable, and located below the working plate 42. The lid portion 20A is provided so that the surface thereof is coincident with the surface of the working plate 42 and thus serves as a part of the working plate 42. The end 47A of the door mount recess portion 47 is located at the incubator 21 side with respect to the centrifugal machine 20 so that it does not disturb the arrangement of the centrifugal machine 20.

The exhaust hole portions 45 extend in a belt-like arrangement in the width direction of the glove box 11 along the front and rear edges of the working plate 42, and plural holes having substantially the same diameter are formed to penetrate through the working plate 42 and arranged to be spaced from one another at a substantially equal interval. The exhaust hole portions 45 are provided to the front and rear edges of the working plate 42, and thus they are prevented from obstructing the cultivating work and the auxiliary work. Here, the exhaust hole portions 45 may be provided by directly forming holes in the working plate 42 or by providing punching metal or a mesh-like plate at the front and rear edge portions of the working plate 42.

Furthermore, the upper duct 46B and the lower duct 46A are provided over the whole area in the width direction of the glove box 11.

Each of the exhaust hole portion 45 is configured to have an operation area side exhaust hole portion 45A provided in the operation area 25 (an exhaust hole portion at the operation area side), and an auxiliary working area side exhaust hole portion 45B provided in the auxiliary working area 35 (an exhaust hole portion at the auxiliary working area side).

The operation area side exhaust hole portion 45A is provided so that a part thereof is overlapped with the door mount recess portion 47, and no hole is formed at the overlap portion thereof with the door mount recess portion 47. Specifically, the operation area side exhaust hole portion 45A at the rear edge side is provided only around (particularly, in the neighborhood) of the boundary portion S. In the operation area side exhaust hole portion 45A at the front edge side, the operation area side exhaust hole portion 45A is provided to be continuous from the boundary portion S to the incubator 21 side. However, in the operation area side exhaust hole portion 45A, the number of holes located along the door mount recess portion 47 is set to be smaller than the number of holes located at the other portions.

Furthermore, the auxiliary working area side exhaust hole portions 45B are provided to be continuous from the boundary portion S to the pass box 22 side (FIG. 1) at both the front and rear edges.

That is, in the auxiliary working area side exhaust hole portions 45B, a larger number of holes are formed than that in the operation area side exhaust hole portions 45A. Therefore, in the exhaust hole portions 45, the total opening space (the total area of the opening) of the holes in the auxiliary working area side exhaust hole portions 45B is larger than the total opening space of the holes in the operation area side exhaust hole portions 45A. Therefore, air (gas) more easily flows into the working chamber 16 at the auxiliary working area side exhaust hole portion 45B side than that at the operation area side exhaust portion 45A. Therefore, in the working chamber 16, air (gas) flows from the operation area 25 side at the upstream side to the auxiliary working area 35 side at the downstream side. That is, air (gas) flow in the working chamber 16 is controlled by the exhaust hole portions 45, and the exhaust hole portions 45 function as an air (gas) flow control unit.

Next, the air (gas) flow in the working chamber 16 will be described. In FIGS. 1, 2 and 4, the flow of air (gas) is represented by an arrow X.

As shown in FIG. 1, fresh air is supplied from the air supply chamber 33 extending in the width direction into the whole area in the width direction of the working chamber 16. This air flows downwardly as if it is attracted by the front and rear exhaust hole portions 45.

As shown in FIG. 1, the downwardly flowing air flow straightly downwardly in the auxiliary working area 35, and flows into each of the front and rear auxiliary working area side exhaust hole portions 45B. In the operation area 25, most of the downwardly flowing air flows straightly downwardly to the neighborhood of the gloves 19A, 19B. Below the gloves 19A, 19B, the flow of the air is bent to the auxiliary working area 35 side around (particularly, in the neighborhood of the working plate 42) as if the air is attracted to the auxiliary working area side exhaust hole portions 45B, and then the air flows into each of the auxiliary working area side exhaust hole portions 45B. A part of the air flowing in the operation area 25 flows into the operation area side exhaust hole portions 45A. Thereafter, the air flowing into the auxiliary working area side exhaust hole portions 45B and the operation area side exhaust hole portions 45A is passed through the lower duct 46A and the upper duct 46B and discharged from the exhaust blower 14 to the outside.

As described above, in the glove box 11, the total opening area of the holes of the auxiliary working area side exhaust hole portions 45B is set to be larger than the total opening area of the holes of the operation area side exhaust hole portion 45A, whereby the air flows from the operation area 25 side to the auxiliary working area 35 side. Therefore, even when dust has already occurred when the auxiliary work is performed at the auxiliary working area 35 side, this dust is made to flow to the auxiliary working area side exhaust hole portions 45B by the air flowing to the auxiliary working area 35 side. Accordingly, dust can be prevented from contaminating into the place at the operation area 25 side at which the cultivating work is performed.

Furthermore, in the operation area 25, the air flowing downwardly to the neighborhood of the gloves 19A and 19B is attracted by the auxiliary working area side exhaust hole portions 45B, and the air flow is bent to the auxiliary working area 35 side around the working plate 42 below the gloves 19A, 19B. Therefore, the air is made to flow from the upper side to the lower side while the air is supplied as uniformly as possible, and the air flow is bent to the auxiliary working area 35 side around the working plate 42, thereby preventing contamination of dust.

Furthermore, two workers can simultaneously perform a work in the operation area 25 and the auxiliary working area 35 respectively while sharing the work by using the gloves 19A, 19B and the gloves 19C, 19D, respectively. Therefore, the working efficiency can be enhanced, and also even when a package for an instrument or the like is opened in the auxiliary working area 35, dust caused by the package can be prevented from contaminating into the operation area 25.

As described above, according to the first embodiment to which the present invention is applied, the air flowing from the upper side to the lower side in the operation area and the auxiliary working area 35 is controlled to flow from the operation area 25 side to the auxiliary working area 35 side around (particularly, in the neighborhood of) the gloves 19A and 19B by the auxiliary working area side exhaust hole portions 45B of the exhaust hole portions 45. Therefore, air (gas) can be made to flow from the operation area 25 side to the auxiliary working area 35 side while uniformly supplied into the working chamber 16. Accordingly, dust caused by a package opened at the auxiliary working area 35 side is made to flow to the auxiliary working area side exhaust hole portions 45B by the air (gas) stream from the operation area 25 side to the auxiliary working area 35 side, so that scattering of dirt and dust to the operation area 25 side can be prevented, and they can be prevented from affecting the cultivating work such as the operation, etc. of cells.

Furthermore, the air flow is controlled by the exhaust hole portions 45 provided to the working plate 42 in the operation area 25 and the auxiliary working area 35. Therefore, the air (gas) flow can be controlled so that the air (gas) flows to the auxiliary working area 35 side around (particularly, in the neighborhood of) the working plate 42, so that the air (gas) can be made to flow from the operation area 25 side to the auxiliary working area 35 side while the air (gas) is made to flow from the upper side to the lower side to uniformly supply the air (gas) into the working chamber 16. Furthermore, the total opening area of the holes at the auxiliary working area 35 side is set to be larger than the total opening area of the holes at the operation area 25 side, whereby the air flow can be controlled. Accordingly, it is not required to provide any dedicated part for controlling the air flow, and the structure can be simplified.

Furthermore, the incubator 21 is provided at the operation area 25 side, and thus cells operated in the operation area 25 can be easily taken out from the operation area 25 and put into the incubator 21. Therefore, the workability is excellent. Furthermore, contamination of dirt or dust into the incubator 21 can be prevented.

The first embodiment is a mere embodiment of the present invention, and thus the present invention is not limited to the first embodiment.

In the first embodiment, the inside of the working chamber 16 is sectioned into the operation area 25 and the auxiliary working area 35. However, the present invention is not limited to this style, and the inside of the working chamber 16 may be sectioned into at least the operation area 25 and the auxiliary working area 35. For example, a storage area for storing instruments, etc. may be provided adjacently to the auxiliary working area 35. Furthermore, in the first embodiment, dirt and dust are caused by opening the packages. However, the present invention is not limited to this style. For example, dirt and dust may invade into the working area when the pass box 22 is opened. Still furthermore, in the first embodiment, the air supply port 46C corresponds to the lower end of the upper duct 46B connected to the exhaust blower 14. However, the present invention is not limited to this style, and the air supply port may be an intercommunication port intercommunicating with a gas exhausting unit. For example, the air supply port may be an intercommunication port between the exhaust hole portion 45 and a duct connected to the exhaust unit such as an exhaust blower or the like provided to the outside of the isolator 10.

The other detailed constructions may be arbitrarily changed.

Second Embodiment

A second embodiment to which the present invention is applied will be described with reference to FIG. 5. In this embodiment, the same elements as the first embodiment are represented by the same reference numerals, and the description thereof is omitted.

The second embodiment is different from the first embodiment in that the door mount recess portion 47 of the first embodiment is not provided.

Figure 5:
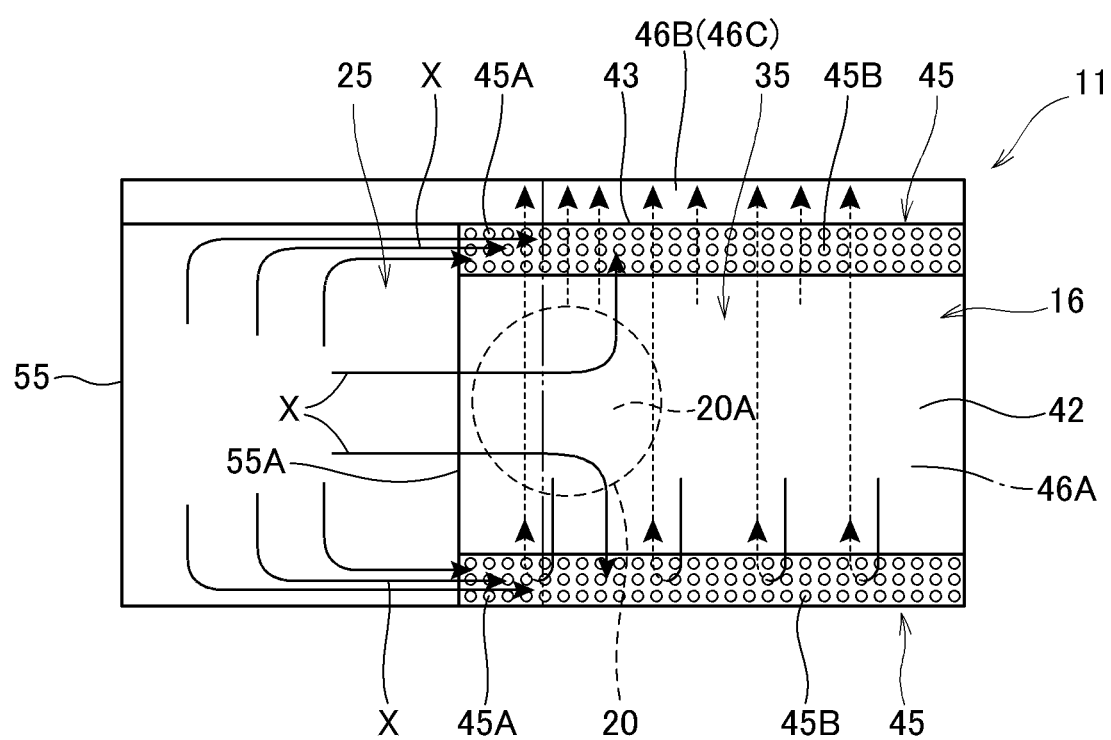
FIG. 5 is a top view of the inside of a working chamber according to a second embodiment.

FIG. 5 is a top view of the inside of a working chamber 16 according to the second embodiment.

In the second embodiment, the joint box door (not shown) of the first embodiment is laterally (horizontally) opened, and thus it is turned to the display 26 side to be opened, so that the door mount recess portion 47 of the first embodiment is not provided to the working plate 42. The working plate 42 has an operation area side working face 55 extending to the incubator 21 side. The operation area side working face 55 is formed to that the surface thereof is coincident with the surface of the working plate 42 in the auxiliary working area 35, and no exhaust hole portion 45 is formed on the operation area side working face 55. The end 55A of the operation area side working face 55 is located at the incubator 21 side with respect to the centrifugal machine 20. The cultivating work is mainly performed on the operation area side working face 55.

The operation area side exhaust hole portion 45A is provided only around (particularly, in the neighborhood of) the boundary portion S on the working plate 42. Furthermore, the auxiliary working area side exhaust hole portion 45B is continuously provided from the boundary portion S till the pass box 22 side (FIG. 1).

As described above, the operation area side working face 55 having no exhaust hole portion 45 is provided in the operation area 25, whereby the total opening area of the holes of the auxiliary working area side exhaust hole portions 45B can be set to be relatively larger than the total opening area of the holes of the operation area side exhaust hole portions 45A and thus the air flow can be controlled so that air flows form the operation area 25 to the auxiliary working area 35.

Third Embodiment

A third embodiment to which the present invention is applied will be described hereunder with reference to FIG. 6. In the third embodiment, the same constituent elements as the first embodiment are represented by the same reference numerals, and the description thereof is omitted.

The third embodiment is different from the first embodiment in that the area of the exhaust hole portion 145 varies continuously.

Figure 6:
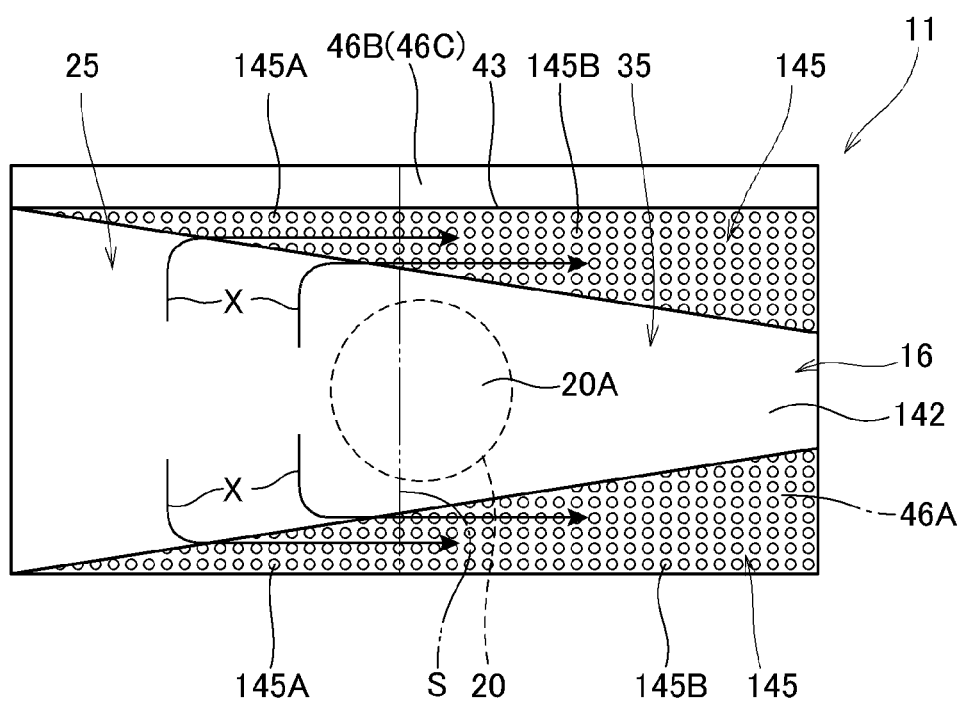
FIG. 6 is a top view of the inside of a working chamber according to a third embodiment.

FIG. 6 is a top view showing the inside of the working chamber 16 according to the third embodiment.

In the third embodiment, a working plate 142 (lower surface) extending from the incubator 21 side to the pass box 22 side is provided in place of the working plate 42 of the first embodiment. In the third embodiment, the joint box door (not shown) shown with respect to the first embodiment is designed to be laterally opened, and the upper surface of the working plate 142 is formed to be flat over the whole surface thereof.

The exhaust hole portions 145 extends in the width direction of the glove box 11 along the front and rear edges of the working plate 142 respectively, and each of the exhaust hole portions 145 is formed in a belt-like shape so that the width thereof gradually increases from the incubator 21 side to the pass box 22 side. In plan view, each exhaust hole portion 145 is formed in a triangular shape to be tapered from the pass box 22 side to the incubator 21 side. That is, the total opening area of the holes of the auxiliary working area side exhaust hole portions 145B formed at the auxiliary working area 35 side is set to be larger than the total opening area of the holes of the operation area side exhaust hole portions 145A formed at the operation area 25 side.

As described above, by continuously varying the area of the exhaust hole portion 145, the total opening area of the holes of the auxiliary working area side exhaust hole portions 145B may be set to be larger than the total opening area of the holes of the operation area side exhaust hole portions 145A, whereby air flow is controlled so that air flows from the operation area 25 to the auxiliary working area 35.

Fourth Embodiment

A fourth embodiment to which the present invention is applied will be described with reference to FIG. 7. In the fourth embodiment, the same constituent elements as the first embodiment are represented by the same reference numerals, and the description thereof is omitted.

In the fourth embodiment, the shape of an upper duct 146 continuous with the lower duct 46A and the shape of the air supply port 146C at the lower end of the upper duct 146B are different from the shapes of the upper duct 46 and the air supply port 46C of the first embodiment.

Figure 7:
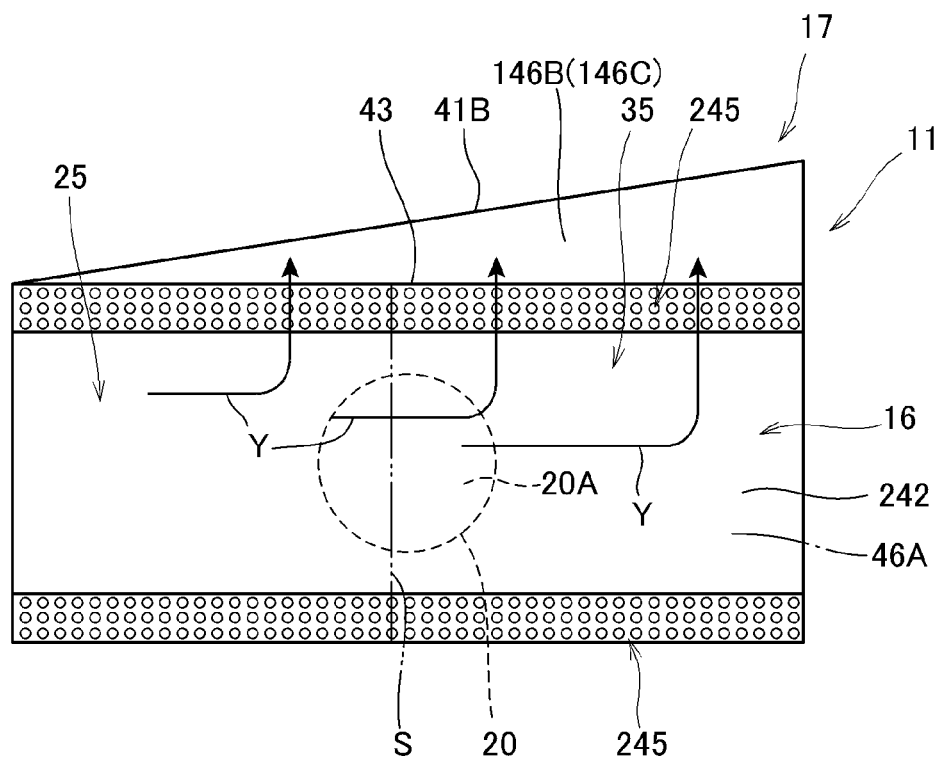
FIG. 7 is a top view of the inside of a working chamber according to a fourth embodiment.

FIG. 7 is a top view of the inside of the working chamber 16 according to the fourth embodiment.

In the fourth embodiment, a working plate 242 (lower surface) extending from the incubator 21 side to the pass box 22 side is provided in place of the working plate 42 of the first embodiment. Furthermore, in the fourth embodiment, the joint box door (not shown) shown in FIG. 1 is designed to be laterally opened, and the upper surface of the working plate 242 is formed to be flat over the whole surface thereof.

Exhaust hole portions 245 extend over the whole length in the width direction of the glove box 11 along the front and rear edges of the working plate 242 respectively, and each of the exhaust hole portion 245 is formed in a belt-like shape to be uniform in width over the whole length thereof.

In the fourth embodiment, the upper duct 146 and the air supply port 146C of the upper duct 146B between the back surface 41B of the housing 17 and the back surface plate 43 of the inner wall plate 40 (FIG. 2) are designed to be gradually expanded in the depth direction of the glove box 11 from the incubator 21 side to the pass box 22 side. Therefore, air (gas) in the working chamber 16 easily flows to the pass box 22 side, and the air flows from the operation area 25 side to the auxiliary working area 35 side as indicated by arrows Y in FIG. 7. As described above, the size of the upper duct 146B is gradually increased while shifting from the operation area 25 side to the auxiliary working area 35 side, whereby air flow is controlled so that air (gas) flows to the auxiliary working area 35 side.

Fifth Embodiment

A fifth embodiment to which the present invention is applied will be described with reference to FIG. 8.

In this fifth embodiment, the same constituent elements as the first embodiment are represented by the same reference numerals, and the description thereof is omitted.

In the fifth embodiment, the shape of the upper duct 246B continuous with the lower duct 46A and the shape of the air supply port 246C at the lower end of the upper duct 246 are different from the shapes of the upper duct 46B and the air supply port 46C of the first embodiment.

Figure 8:
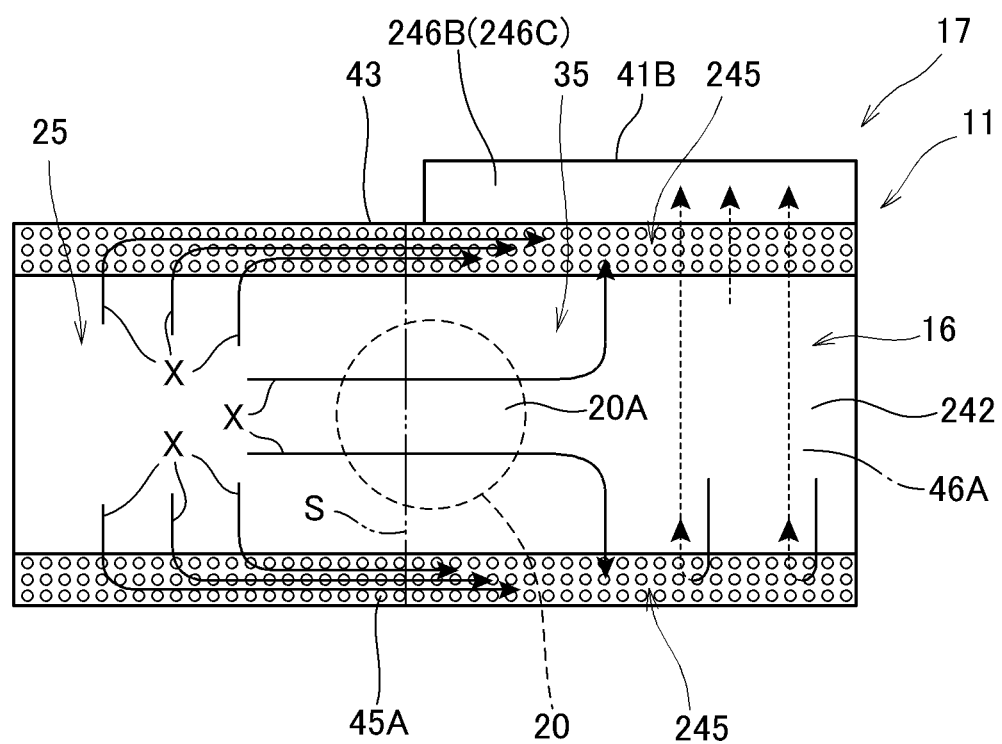
FIG. 8 is a top view of the inside of a working chamber according to a fifth embodiment.

FIG. 8 is a top view of the inside of the working chamber 16 according to the fifth embodiment.

In the fifth embodiment, the working plate 242 extending from the incubator 21 side to the pass box 22 side is provided in place of the working plate 42 of the first embodiment. Furthermore, in the fifth embodiment, the joint box door (not shown) described with reference to the first embodiment is designed to be laterally opened, and the upper surface of the working plate 242 is formed to be flat over the whole surface thereof.

The exhaust hole portions 245 extend over the whole length in the width direction of the glove box 11 along the front and rear edges of the working plate 242 respectively, and each of the exhaust hole portions 245 which is formed in a belt-like shape is formed to be uniform in width over the whole length thereof.

In the fifth embodiment, the upper duct 246B and the air supply port 246C thereof between the back surface 41B of the housing 17 and the back surface plate 43 of the inner wall plate 40 (FIG. 2) are formed only at the auxiliary working area 35 side. Accordingly, air (gas) in the working chamber 16 easily flows to the auxiliary working area 35 side, and air (gas) flows from the operation area 25 side to the auxiliary working area 35 side as indicated by arrows X in FIG. 8. As described above, the exhaust passage 246 at the back surface 41B side is disposed to be tilted to the auxiliary working area 35 side, whereby the air flow is controlled so that air (gas) flows to the auxiliary working area 35 side.

In the fifth embodiment, the upper duct 246B is formed at only the auxiliary working area 35 side. However, the upper duct 246B may be disposed to be tilted to the auxiliary working area 35 side, and a part of the upper duct 246B may be provided in the operation area 25.

Sixth Embodiment

A sixth embodiment to which the present invention is applied will be described with reference to FIGS. 9 to 12. In the sixth embodiment, the same constituent elements as the first embodiment are represented by the same reference numerals, and the description thereof is omitted.

The sixth embodiment is different from the first embodiment in that the air supply blower 13 is provided at the operation area 25 side and the exhaust blower 14 is provided at the auxiliary working area 35 side.

Figure 9:
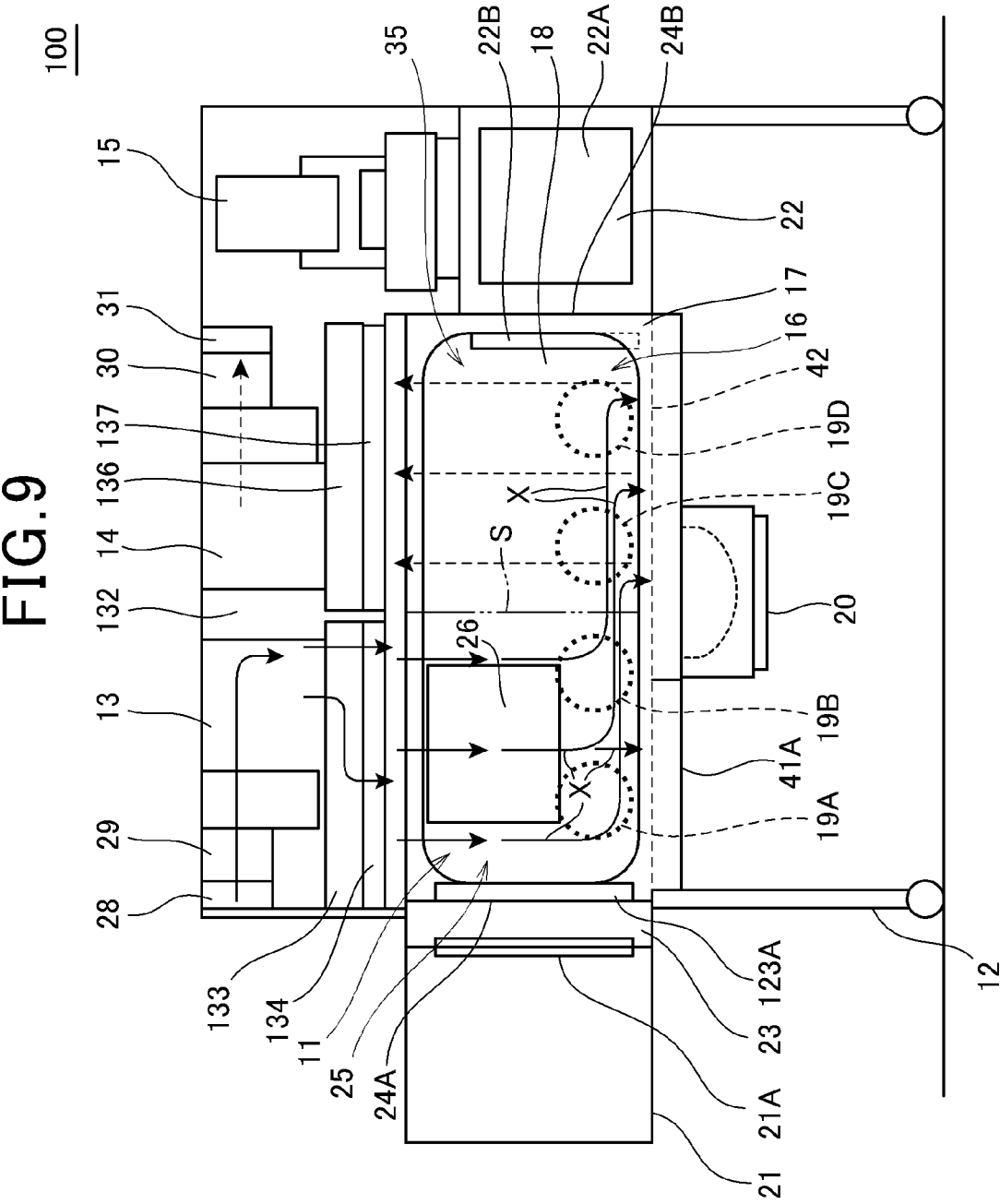
FIG. 9 is a top view of the inside of a working chamber according to a sixth embodiment.
Figure 10:
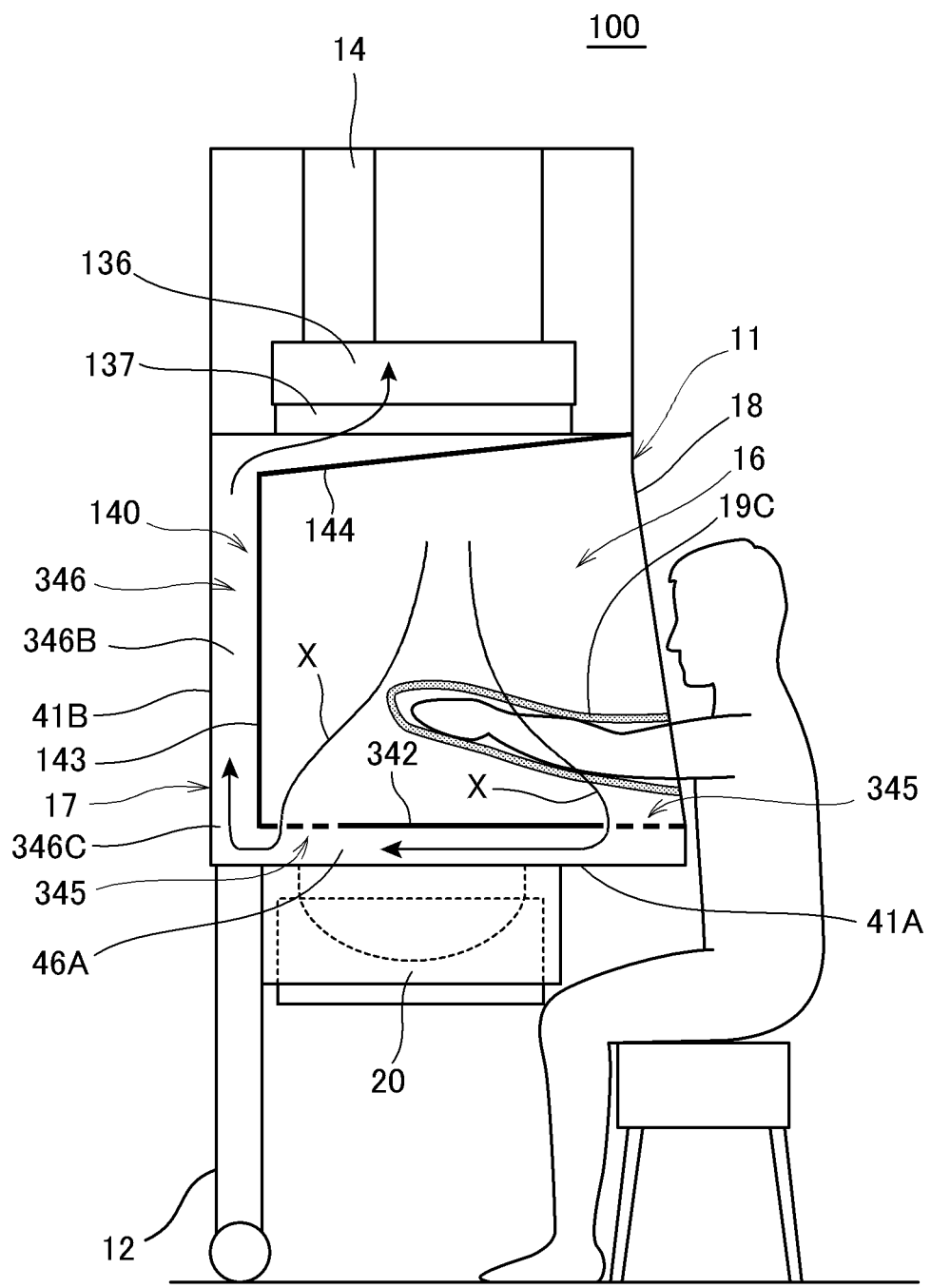
FIG. 10 is a side cross-sectional view of the isolator.

FIG. 9 is a front view showing an isolator 100 according to the sixth embodiment. FIG. 10 is a side cross-sectional view of the isolator 100. Specifically, FIG. 10 is a side cross-sectional view at the auxiliary working area 35 side.

The incubator 21 is provided to one end side of the glove box 11 through the joint box 23, and the joint box 23 is provided with a laterally-opening type joint box door 123A which is turned to the display 26 side and opened.

As shown in FIGS. 9 and 10, the isolator 100 has the glove box 11, and the air supply blower 13 and the exhaust blower 14 are separated from each other in the width direction of the glove box 11 by a partition member 132 provided at the intermediate portion in the width direction of the glove box 11. The partition member 132 is located just above the boundary portion S.

An air supply chamber 133 and an air supply filter 134 which extend from one side in the width direction of the glove box 11 to the partition member 132 are connected to the air supply blower 13. The air supply filter 134 is provided between the air supply chamber 133 and the working chamber 16. Furthermore, an exhaust chamber 136 and an exhaust filter 137 which extend from the partition member 132 to the other end in the width direction of the glove box 11 are provided to the exhaust blower 14. The exhaust filter 137 is provided between the exhaust chamber 136 and the working chamber 16.

That is, in the isolator 100, air (gas) is supplied from the air supply blower 13 at the upper side of the operation area 25 side into the working chamber 16, and then discharged from the exhaust blower at the upper side of the auxiliary working area 35 to the outside.

Furthermore, the air supply filter 134 and the exhaust filter 137 are configured to be attachable/detachable to/from the front surface side of the isolator 100. As described above, in the sixth embodiment, the air supply blower 13 and the exhaust blower 14 are arranged side by side in the width direction of the glove box 11, and configured to be attachable/detachable to/from the front surface side of the isolator 100, so that the maintenance performance is excellent.

As shown in FIG. 10, an inner wall plate 140 which extends wholly in the width direction of the glove box 11 and partitions the inside of the glove box 11 is provided in the glove box 11, and a space is formed at the lower portion and the back surface portion of the inside of the glove box 11 by the inner wall plate 140. The inner wall plate 140 has a working plate 342 (lower surface) constituting the bottom surface portion of the working chamber 16 which is disposed to be spaced from the bottom surface 41A of the housing 17, a back surface plate 143 which is provided to be spaced from the back surface 41B of the housing 17 and constitutes the back surface of the working chamber 16, and a partition plate 144 for connecting the upper end of the back surface plate 143 and the upper surface of the working chamber 16.

Figure 11:
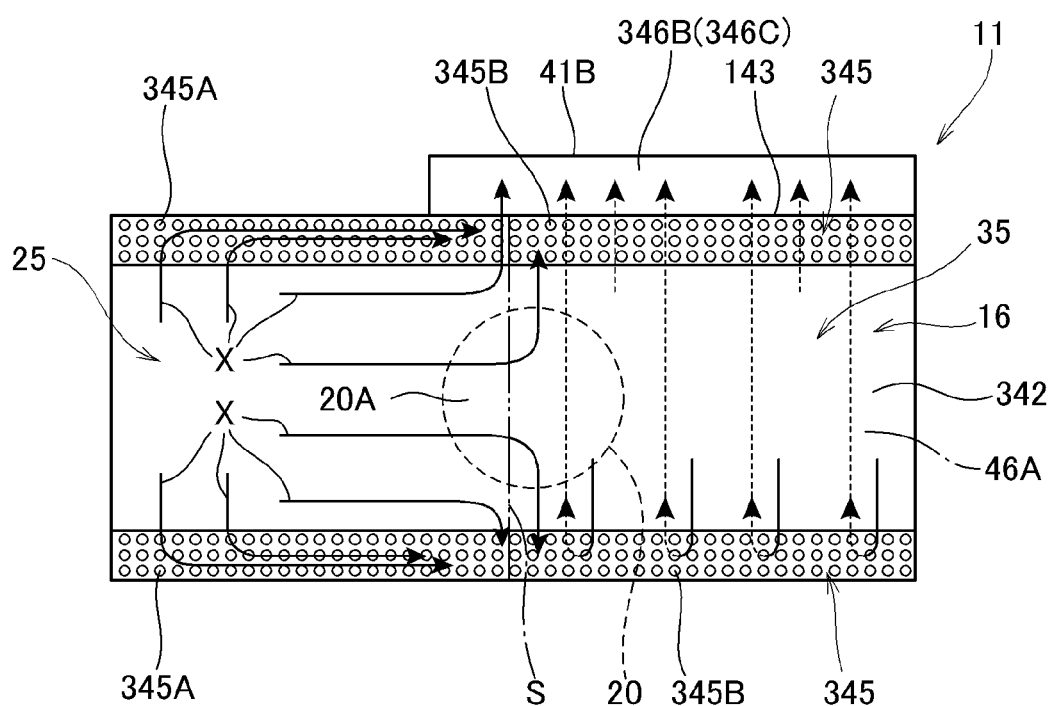
FIG. 11 is a top view of the inside of the working chamber.

FIG. 11 is a top view of the inside of the working chamber 16.

As shown in FIGS. 10 and 11, the working plate 342 is provided substantially in parallel to the bottom surface 41A, and the front and rear edges thereof are provided with exhaust hole portions 345 extending in the width direction of the glove box 11. The back surface plate 143 is provided to be tilted to the auxiliary working area 35 side and continuous with the rear edge of the working plate 342 and extends upwardly in parallel to the back surface 41B of the rear edge of the working plate 342. The partition plate 144 obliquely extends from the upper edge of the back surface plate 143 to the front surface side, and is connected to the front edge of the upper surface of the working chamber 16. The partition plate 144 is provided so as to cover the exhaust filter 137 from the lower side.

The space surrounded by the working plate 342, the back surface plate 143, the partition plate 144, and the bottom surface 41A and the back surface 41B of the housing 17 functions as an exhaust passage 346, and exhaust gas from the working chamber 16 passes through the exhaust passage 346 and flows into the exhaust blower 14. The exhaust passage 346 has a lower duct 46A passing below the working plate 342, and an upper duct 346B (exhaust duct) extending upwardly between the back surface 41B of the housing 17 and the back surface plate 143 and intercommunicating with the exhaust filter 137. The upper duct 346B intercommunicates with the working chamber 16 through only the lower duct 46A and the exhaust hole portions 345. The lower end of the upper duct 346 serves as an air supply port 346C of the upper duct 346B.

The air supply filter 134 is not covered by the upper duct 346B, and the air supply blower 13 is directly connected to the inside of the working chamber 16 through the air supply filter 134.

In the sixth embodiment, the upper duct 346B connected to the exhaust blower 14 and the air supply port 346C at the lower end of the upper duct 346B are provided to be tilted to the auxiliary working area 35, and thus air (gas) in the working chamber 16 flows from the operation area 25 side to the auxiliary working area 35 side. That is, the air (gas) flow in the working chamber 16 is controlled on the basis of the position of the upper duct 346, and the upper duct 346B functions as an air (gas) flow control unit.

As shown in FIG. 11, each exhaust hole portion 345 has plural holes of substantially the same diameter which are formed so as to be arranged at a substantially equal interval, and is designed in a belt-like shape having substantially the same width over the whole width of the working chamber 16.

Each exhaust hole portion 345 has an operation side exhaust hole portion 345A provided to the operation area 25, and an auxiliary working side exhaust hole portion 345B provided to the auxiliary working area 35. Each exhaust hole portion 345 has substantially the same width over the whole width of the working chamber 16, and thus the total opening area of the holes of the operation side exhaust hole portions 345A is equal to the total opening area of the holes of the auxiliary working side exhaust hole portions 345B. Here, the total opening area is equal between the operation side exhaust hole portions 345A and the auxiliary working side exhaust hole portions 345B are equal to each other, and this indicates that the total opening areas of the operation side exhaust hole portions 345A and the auxiliary working side exhaust hole portions 345B is equal to each other to the extent that the difference therebetween does not affect the air (gas) flow.

Next, the air (gas) flow in the working chamber 16 will be described with reference to FIGS. 9 to 11. In FIGS. 9 to 11, the air (gas) flow is represented by arrows X.

As shown in FIG. 9, fresh air (gas) is supplied from the air supply chamber 133 through the air supply filter 134 to the upper side of the operation area 25 of the working chamber 16 by the air supply blower 13, and this air downwardly flows as if it is attracted by the front and rear exhaust hole portions 345 as shown in FIG. 10.

As shown in FIGS. 9 and 11, the downwardly flowing air (gas) flows straightly downwardly to the neighborhood of the gloves 19A, 19B as if it is attracted to the operation side exhaust hole portions 345A. The flow of a part of the air (gas) is bent to the auxiliary working area 35 side around (particularly, in the neighborhood of) the working plate 342 as it the air (gas) is attracted to the auxiliary working side exhaust hole portions 345B below the gloves 19A, 19B, and then the air (gas) flows into the auxiliary working side exhaust hole portions 345B. The residual air (gas) directly downwardly flows into the operation side exhaust hole portions 345A. Thereafter, the air (gas) flowing into the auxiliary working side exhaust hole portions 345B and the operation side exhaust hole portions 345A is passed from the lower duct 46A and the air supply port 346C through the upper duct 346B and then discharged from the exhaust blower 14 to the outside.

As described above, according to the sixth embodiment to which the present invention is applied, since the upper duct 346B and the air supply port 346C at the lower end of the upper duct 346B of the exhaust passage 346 for exhausting air (gas) from the working chamber 16 are disposed to be tilted to the auxiliary working area 35 side, air (gas) flows to the upper duct 346B side, and thus the air (gas) can be made to flow from the operation area 25 side to the auxiliary working area 35 side, thereby preventing dirt or dust from being scattered to the operation area 25 side.

Furthermore, the working plate 342 at the operation area 25 side is provided with the operation side exhaust hole portions 345A whose total opening area is equal to that of the auxiliary working side exhaust hole portions 345B, and thus air (gas) flows to the exhaust hole portions 345 of the operation area 25 and the auxiliary working area 35. Therefore, an air (gas) stream flowing from the upper side to the lower side can be formed in the operation area 25 and the auxiliary working area 35, and thus air (gas) can be uniformly supplied to both the operation area 25 and the auxiliary working area 35. The air flow can be controlled with a simple structure that the upper duct 346B is provided to the auxiliary working area 35 side, and thus air (gas) can be made to flow from the operation area 25 side to the auxiliary working area 35 side with a simple structure.

Figure 12:
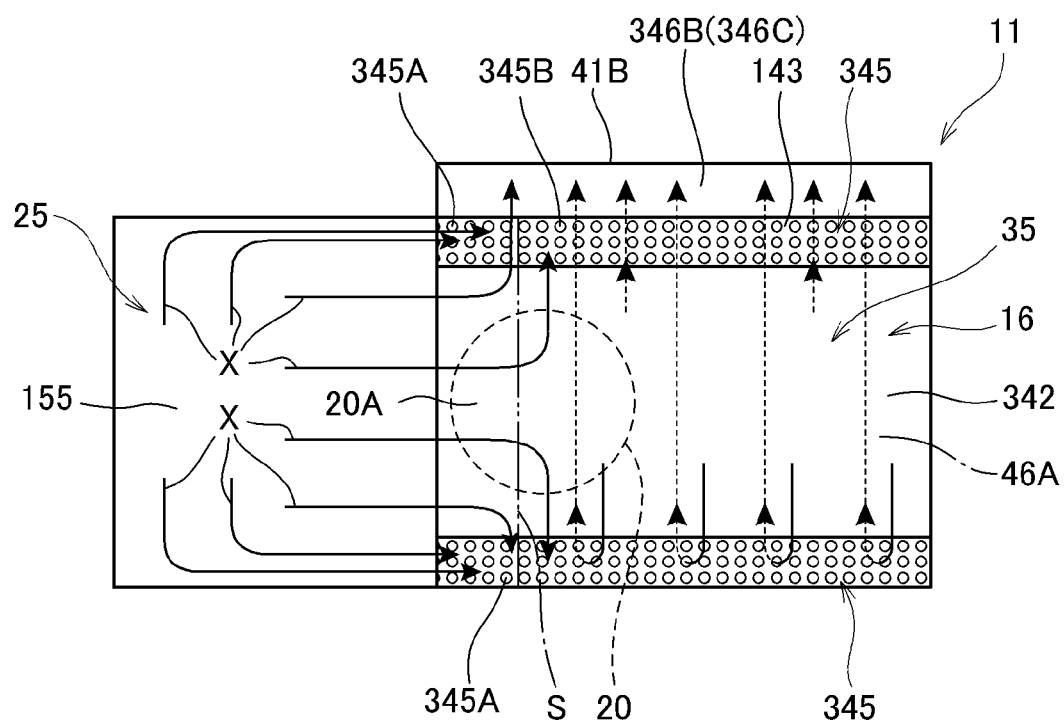
FIG. 12 is another top view of the inside of the working chamber.

In the sixth embodiment, the exhaust hole portions 345 are provided over the whole width of the working chamber 16. However, the present invention is not limited to this embodiment. The exhaust hole portions 345 may be provided to at least the auxiliary working area 35 of the working plate 342. For example, as shown in FIG. 12, an operation area side working face 155 on which no operation side exhaust hole portion 345A is formed may be provided to the working plate 342 at the operation area 25 side. In this case, the air (gas) which is supplied by the air supply blower 13 and downwardly flows into the working chamber 16 is attracted to the upper duct 346B disposed to be tilted to the auxiliary working area 35 side, and flows into the auxiliary working side exhaust hole portions 345B as indicated by arrows X in FIG. 12. Accordingly, the air (gas) can be made to flow from the operation area 25 side to the auxiliary working area 35 side, thereby preventing scattering of the dust to the operation area 25 side.

Furthermore, in the sixth embodiment, the joint box door 123A is configured to be laterally opened. However, the present invention is not limited to this embodiment, and the joint box door 123A may be configured to be downwardly laid to the working chamber 16 side as in the case of the first embodiment. In this case, a recess portion for mounting the joint box door 123A may be provided to the working plate 342, and the joint box door 123A may be used as a working table.

Seventh Embodiment

A seventh embodiment to which the present invention is applied will be described with reference to FIGS. 13 to 16. The same constituent elements as the first embodiment are represented by the same reference numerals, and the description thereof is omitted.

The seventh embodiment is different from the first embodiment in that the exhaust blower 14 is provided below the working chamber 16.

Figure 13:
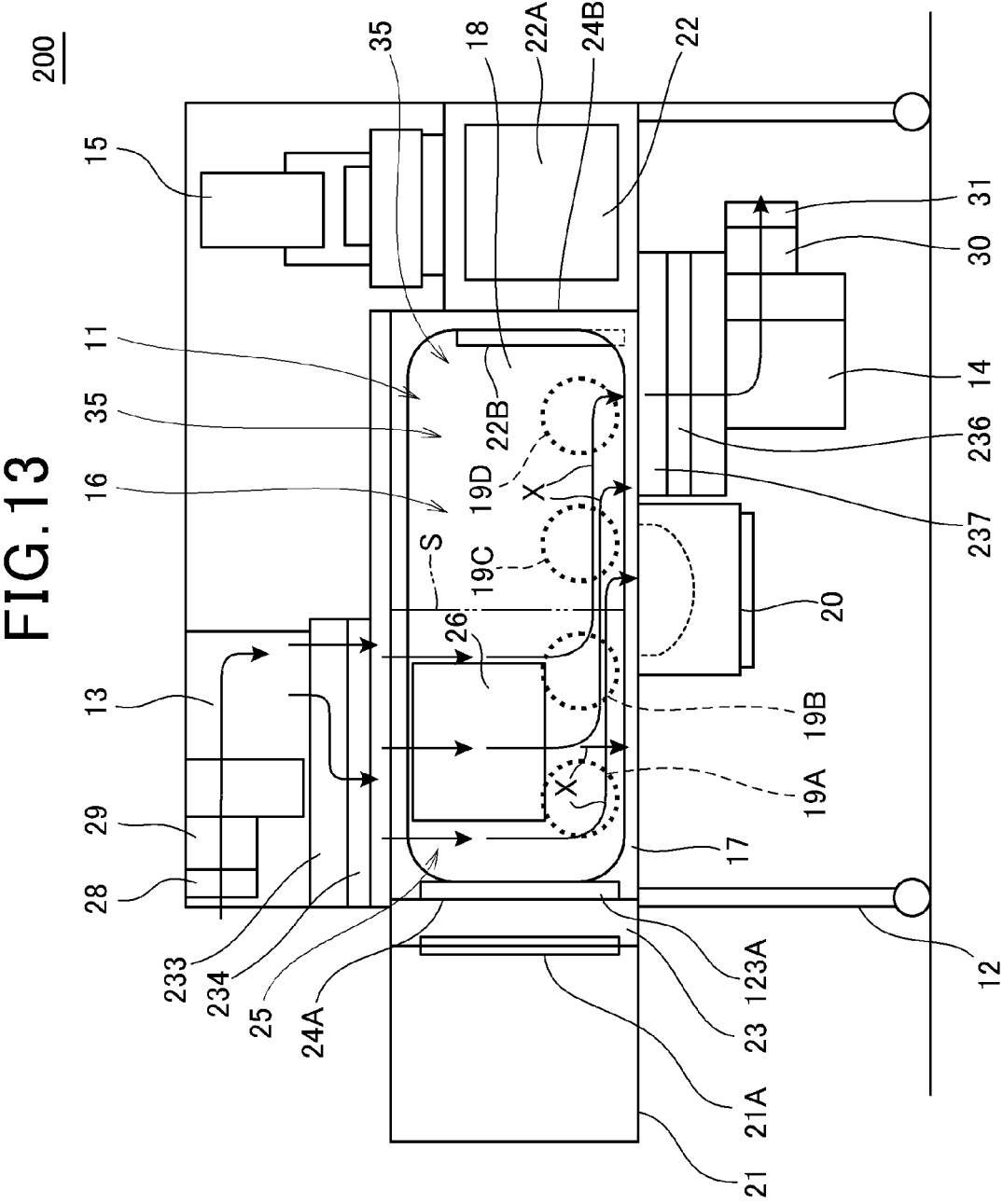
FIG. 13 is a front view showing an isolator according to a seventh embodiment.
Figure 14:
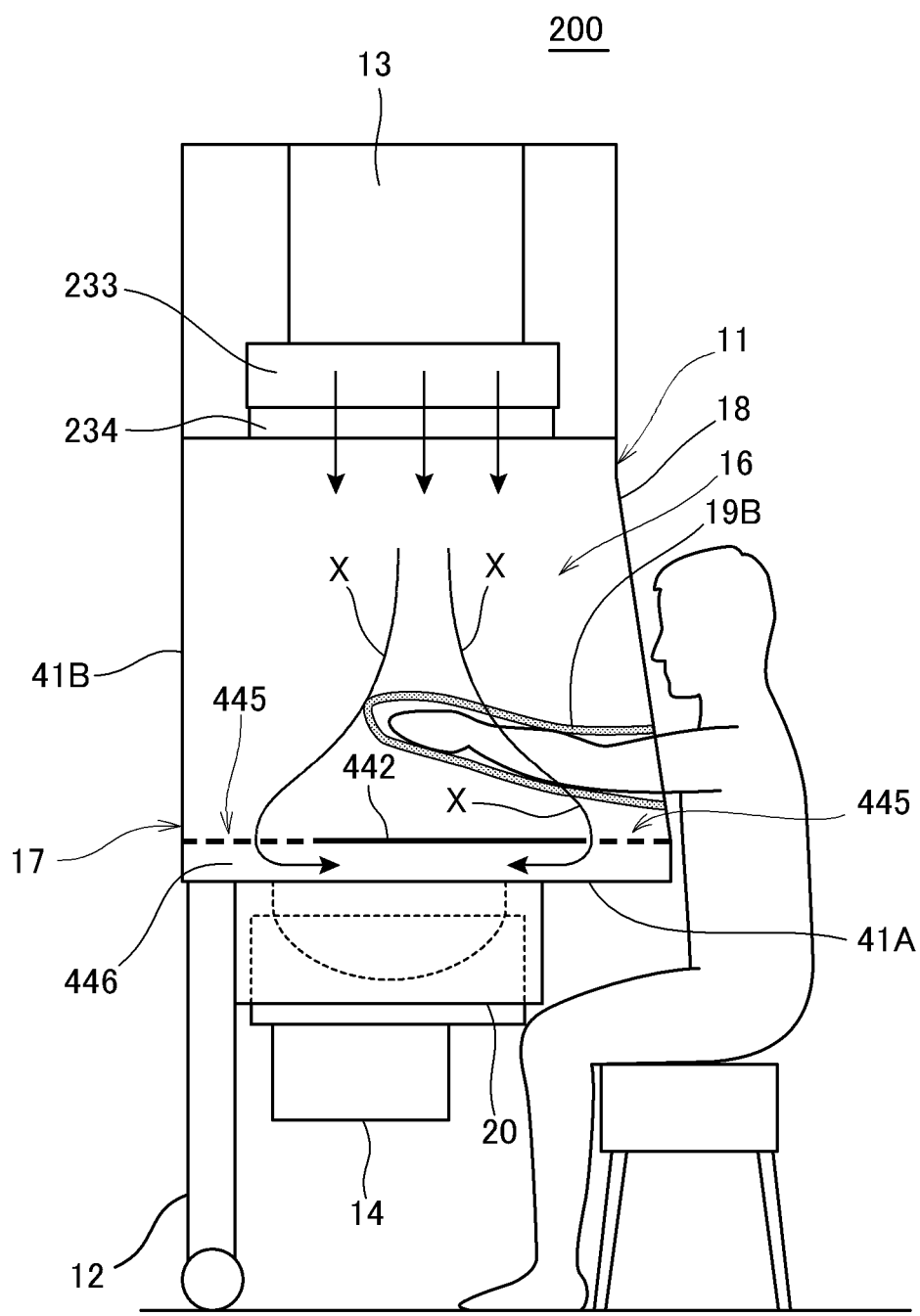
FIG. 14 is a side cross-sectional view showing the isolator.

FIG. 13 is a front view showing an isolator 200 according to the seventh embodiment. FIG. 14 is a side cross-sectional view showing the isolator 200.

The incubator 21 is provided to one end side of the glove box 11 through the joint box 23. The joint box 23 is provided with a joint box door 123A which is designed to be turned to the display 26 side and opened laterally.

As shown in FIGS. 13 and 14, the isolator 200 has the glove box 11, the air supply blower 13 is disposed above the glove box 11 and the exhaust blower 14 is disposed below the glove box 11.

The air supply blower 13 is connected to the working chamber 16 through an air supply chamber 233 and an air supply filter 234. The air supply blower 13, the air supply chamber 233 and the air supply filter 234 are disposed at one side in the width direction of the glove box 11, and it is located at the side of the incubator 21 with respect to the boundary portion S.

Furthermore, the exhaust blower 14 is connected to the bottom surface 41A of the housing 17 from the lower side through an exhaust chamber 236 and an exhaust filter 237 (air supply port). The exhaust blower 14, the exhaust chamber 236 and the exhaust filter 237 are disposed at the other side in the width direction of the glove box 11, and it is located at the side of the pass box 22 with respect to the boundary portion S.

That is, in the isolator 200, air (gas) is supplied from the air supply blower 13 at the upper side of the operation area 25 into the working chamber 16, and then discharged from the exhaust blower 14 at the lower side of the auxiliary working area 35 to the outside. Furthermore, the air supply filter 234 and the exhaust filter 237 are configured to be attachable/detachable to/from the front surface side of the isolator 200, so that the maintenance performance is excellent.

As shown in FIG. 14, a working plate 442 (lower surface) for partitioning the lower portion of the glove box 11 is provided in the glove box 11. The working plate 442 is provided substantially in parallel to the bottom surface 41A of the housing 17 so as to be spaced from the bottom surface 41A of the housing 17, and constitutes the bottom surface of the working chamber 16.

Figure 15:
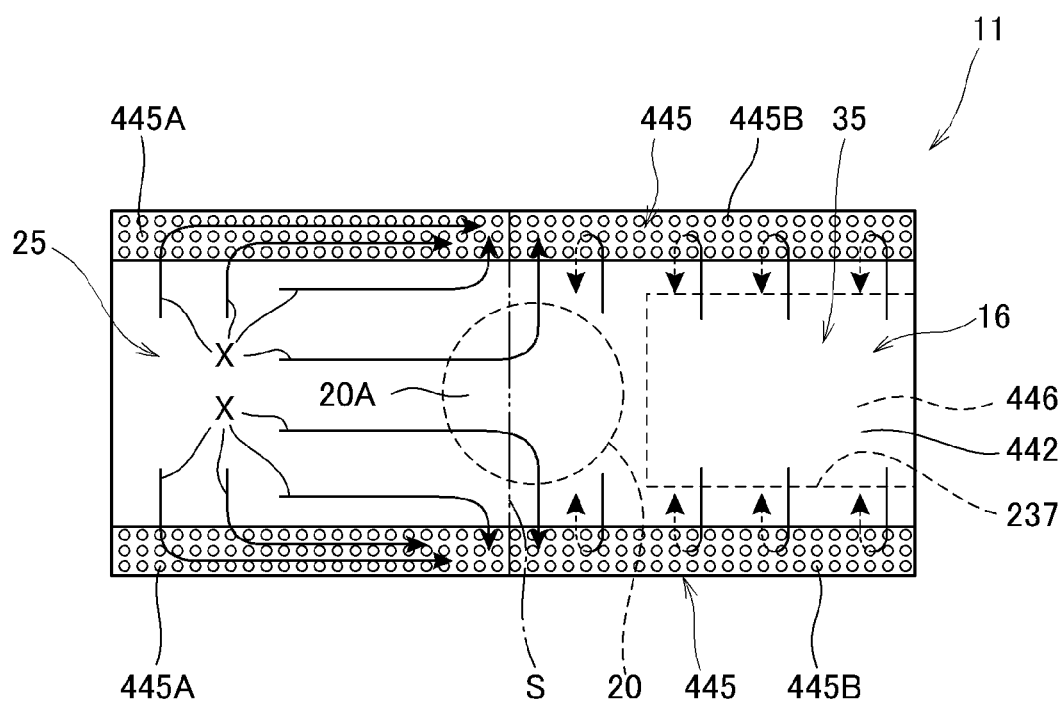
FIG. 15 is a top view showing the inside of the working chamber.

FIG. 15 is a top view of the inside of the working chamber 16.

As shown in FIGS. 14 and 15, the working plate 442 is provided substantially in parallel to the bottom surface 41A, and exhaust hole portions 445 extending in the width direction of the glove box 11 are provided to the front and rear edges of the working plate 442, respectively. An exhaust passage 446 is formed below the working plate 442, and it is formed by a space formed between the bottom surface 41A and the working plate 442. The exhaust passage 446 is connected to the exhaust blower 14 through the exhaust filter 237 provided at the auxiliary working area 35 side. That is, the exhaust filter 237 functions as an air supply port of the exhaust blower 14 in the glove box 11.

As shown in FIG. 15, each exhaust hole portion 445 is designed in a belt-like shape having substantially the same width over the whole width of the working chamber 16, and plural holes having substantially the same diameter are formed in each exhaust hole portion 445 so as to be arranged at a substantially equal interval.

Each exhaust hole portion 445 comprises an operation area side exhaust hole portion 445A provided in the operation area 25, and an auxiliary working area side exhaust hole portion 445B provided in the auxiliary working area 35. Each exhaust hole portion 445 has substantially the same width over the whole width of the working chamber 16, and thus the total opening area of the holes of the operation area side exhaust hole portion 445A is equal to the total opening area of the holes of the auxiliary working area side exhaust hole portion 445B. Here, the total opening area is equal between the operation area side exhaust hole portion 445A and the auxiliary working area side exhaust hole portion 445B, and this indicates that the total opening area is equal between the operation area side exhaust hole portion 445A and the auxiliary working area side exhaust hole portion 445B to the extent that the difference in total opening area therebetween does not affect the air (gas) flow of the working chamber 16.

In the seventh embodiment, the exhaust blower 14 is provided at the auxiliary working area 35 side below the glove box 11, and in connection with this structure, the exhaust filer 237 as the air supply port is connected to the exhaust passage 446 of the auxiliary working area 35. Therefore, air (gas) in the working chamber 16 flows from the operation area 25 side to the auxiliary working area 35 side. That is, the air (gas) flow in the working chamber 16 is controlled on the basis of the position of the exhaust filter 237, and thus the exhaust filter 237 functions as an air (gas) flow control unit.

Next, the air (gas) flow in the working chamber 16 will be described with reference to FIGS. 13 to 15. In FIGS. 13 to 15, the air (gas) flow is represented by arrows X.

As shown in FIG. 13, refresh air (gas) is supplied from the air supply chamber 233 through the air supply filter 234 into the upper portion of the operation area 25 of the working chamber 16. As shown in FIG. 14, this air (gas) flows downwardly as if it is attracted by the front and rear exhaust hole portions 445.

As shown in FIGS. 13 to 15, the downwardly flowing air (gas) flows straightly downwardly to the neighborhood of the gloves 19A, 19B as if it is attracted by the operation area side exhaust hole portions 445A. The flow of a part of the air (gas) is bent to the auxiliary working area 35 side around (particularly, in the neighborhood of) the working plate 442 as if the air (gas) is attracted by the auxiliary working area side exhaust hole portions 445B located below the gloves 19A, 19B, and then the air flows into the auxiliary working area side exhaust hole portions 445B. The residual air (gas) directly flows downwardly and then flows into the operation area side exhaust hole portions 445A. Thereafter, the air (gas) flowing into the auxiliary working area side exhaust hole portions 445B and the operation area side exhaust hole portions 445A is passed through the exhaust passage 446, the exhaust filter 237 and the exhaust chamber 236 and then discharged from the exhaust blower 14.

As described above, according to the seventh embodiment to which the present invention is applied, air (gas) in the working chamber 16 flows to the exhaust filter 237 as the air supply port of the exhaust blower 14 provided below the working plate 442 at the auxiliary working area 35 side. Therefore, the air (gas) flow can be controlled on the basis of the arrangement position of the exhaust blower 14 so that the air (gas) flows from the operation area 25 side to the auxiliary working area 35 side, and scattering of dirt or dust to the operation area 25 side can be prevented by controlling the air (gas) flow in the working chamber 16 with a simple construction.

Furthermore, the operation area side exhaust hole portion 445A and the auxiliary working area side exhaust hole portion 445B are equal to each other in opening area, and air (gas) flows in both the operation area 25 and the auxiliary working area 35, so that an air (gas) stream flowing from the upper side to the lower side can be formed to both the areas and thus air (gas) can be uniformly supplied to both the areas.

Figure 16:
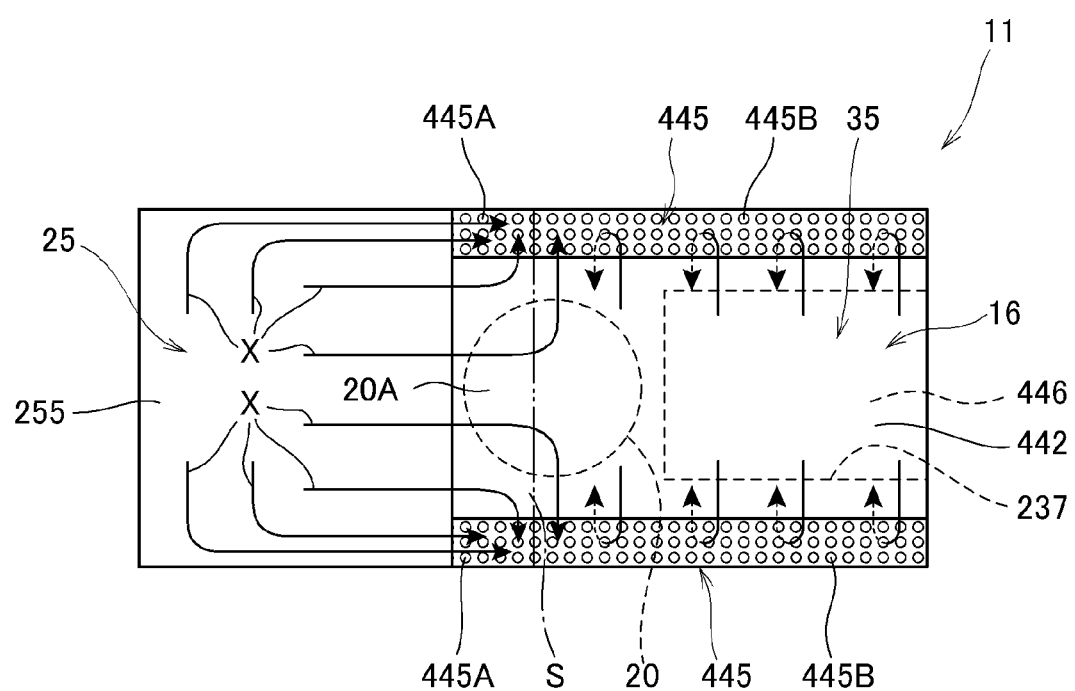
FIG. 16 is another top view of the inside of the working chamber.

In the seventh embodiment, the exhaust hole portions 445 are provided over the whole width of the working chamber 16, however, the present invention is not limited to this style. The exhaust hole portions 445 may be provided to at least the auxiliary working area 35 of the working plate 442. For example, as shown in FIG. 16, an operation area side working face 255 on which no operation area side exhaust hole portion 445A is formed may be provided to the working plate 442 at the operation area 25 side. In this case, the air (gas) which is supplied by the air supply blower 13 and flows downwardly in the working chamber 16 is sucked and attracted to the exhaust filter 237 of the exhaust blower 14 disposed at the auxiliary working area 35 side, and flows into the auxiliary working area side exhaust hole portions 445B as indicated by the arrows X in FIG. 16. Accordingly, air (gas) can be made to flow from the operation area 25 side to the auxiliary working area 35 side, and scattering of dirt and dust to the operation area 25 side can be prevented.

Furthermore, in the seventh embodiment, the joint box door 123A is configured to be laterally opened, however, the present invention is not limited to this style. The joint box door 123A may be configured to be downwardly laid to the working chamber 16 side as in the case of the first embodiment. In this case, the a recess portion in which the joint box door 123A is mounted is provided to the working plate 442, and the joint box door 123A is used as a working table.

What is claimed is:

1. An isolator for cultivating cells, comprising:
   a working chamber having gloves arranged side by side into which operator's hands are inserted to operate cells, the working chamber being sectioned into at least an operation area for operating the cells, and an auxiliary working area for opening a packaged auxiliary instrument used to operate the cells;
   a gas supply blower that supplies gas into the working chamber so that the gas flows downwardly from an upper side in the working chamber;
   an exhaust blower that discharges gas from the working chamber; and
   an exhaust hole portion that is provided at a lower portion of at least the auxiliary working area to constitute a bottom surface of the working chamber, wherein:
   the exhaust hole portion controls flow of the downwardly flowing gas so that flow of the gas is bent to the auxiliary working area from the operation area around the gloves while the gas is discharged from the working chamber through the exhaust hole portion by the exhaust blower.

2. The isolator according to claim 1, wherein the exhaust hole portion is provided to each of the operation area and the auxiliary working area and has an opened area for passing the gas therethrough, and the opened area of the exhaust hole portion at the auxiliary working area side is set to be larger in total opening area than the opened area of the exhaust hole portion at the operation area side.

3. The isolator according to claim 1, further comprising an air supply port that exhausts the gas from the exhaust hole portion and is disposed at the auxiliary working area side.

4. The isolator according to claim 3, wherein the air supply port serves as an air supply port of an exhaust duct for exhausting the gas from the exhaust hole portion.

5. The isolator according to claim 3, wherein the air supply port serves as an air supply port of the exhaust blower, and the exhaust blower is provided below the lower portion of the auxiliary working area.

6. The isolator according to claim 1, wherein the exhaust hole portion is provided to each of the operation area and the auxiliary working area and has an opened area for passing the gas therethrough, and an opening area of the opened area of the exhaust hole portion at the lower portion of the auxiliary working area is set to be equal to the opening area of the opened area of the exhaust hole portion at the operation area side.

7. The isolator according to claim 1, wherein the exhaust hole portion comprises a belt-like member that extends in a width direction of the working chamber and has a plurality of holes formed therein.

8. The isolator according to claim 1, further comprising a cultivating chamber for cell culture that is disposed to be adjacent to the operation area.

9. An isolator for cultivating cells, comprising:
   a working chamber including a plurality of gloves arranged side by side into which operator's hands are inserted to operate cells, an operation area for operating the cells, and an auxiliary working area for opening a packaged auxiliary instrument used to operate the cells;
   a gas supply blower for supplying gas into the working chamber;
   an outlet port provided at an upper portion of the working chamber and configured to supply the gas from the gas supply blower therethrough into the working chamber;
   a gas exhaust blower for exhausting gas from the working chamber; and
   a gas exhaust portion provided at a lower portion of the working chamber and configured to exhaust the gas in the working chamber therethrough,
   wherein the gas exhaust portion at the auxiliary working area is set to be larger in a total opening area than the exhaust portion at the operation area so that the gas flows downwardly from an upper side and bends to an auxiliary working area side from the operation area side in the working chamber.

10. The isolator according to claim 9, further comprising an inlet port disposed at the auxiliary working area side to suck the gas exhausted from the exhaust portion.

11. The isolator according to claim 10, further comprising an exhaust duct connected to the inlet port,
    wherein the gas exhaust blower is connected to the exhaust duct, and the gas is exhausted through the exhaust duct by the gas exhaust blower.

12. The isolator according to claim 10, wherein:
    the exhaust blower is provided below a lower portion of the auxiliary working area and connected to the inlet port, and
    the gas is exhausted through the inlet port by the gas exhaust blower.

13. The isolator according to claim 9, wherein the exhaust portion comprises a plurality of holes arranged in a width-direction of the working chamber.

14. The isolator according to claim 9, further comprising a cultivating chamber that is disposed to be adjacent to the operation area for cell cultures.

15. An isolator for cultivating cells, comprising:
- a working chamber including a plurality of gloves arranged side by side into which operator's hands are inserted to operate cells, an operation area for operating the cells, and an auxiliary working area for opening a packaged auxiliary instrument used to operate the cells;
- a gas supply unit including an outlet port provided at an upper portion of the working chamber and configured to supply the gas into the working chamber through the outlet port; and
- a gas exhaust unit including an exhaust portion provided at a lower portion of the working chamber and an inlet port for sucking the gas exhausted from the exhaust portion, the gas exhaust unit being configured to exhaust the gas from the inlet port,
- wherein the inlet port is disposed at an auxiliary working area side to make the gas flow downwardly from an upper side and bend from the operation area side to the auxiliary working area side.

16. The isolator according to claim 15, wherein the gas exhaust unit further includes an exhaust duct connected to the inlet port, and an exhaust blower connected to the exhaust duct for exhausting the gas through the exhaust duct.

17. The isolator according to claim 15, wherein the gas exhaust unit further includes an exhaust blower connected to the inlet port and configured to exhaust the gas from the inlet port, wherein the exhaust blower is provided below a lower portion of the auxiliary working area.

18. The isolator according to claim 15, wherein the exhaust portion comprises a plurality of holes arranged in a width-direction of the working chamber.

19. The isolator according to claim 15, further comprising a cultivating chamber disposed to be adjacent to the operation area for cell cultures.

20. The isolator according to claim 15, wherein the exhaust portion is provided to each of the operation area and the auxiliary working area, and an opening area of the exhaust portion at the auxiliary working area is equal to the opening area of the exhaust portion at the operation area.

* * * * *